US010285690B2

(12) United States Patent
Nicholas

(10) Patent No.: US 10,285,690 B2
(45) Date of Patent: May 14, 2019

(54) SURGICAL INSTRUMENTS AND SWITCH ASSEMBLIES THEREOF

(71) Applicant: Covidien LP, Mansfield, MA (US)

(72) Inventor: David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/367,879

(22) Filed: Dec. 2, 2016

(65) Prior Publication Data

US 2017/0172568 A1 Jun. 22, 2017

Related U.S. Application Data

(60) Provisional application No. 62/271,081, filed on Dec. 22, 2015.

(51) Int. Cl.
| | |
|---|---|
| H01H 9/02 | (2006.01) |
| A61B 17/068 | (2006.01) |
| A61B 17/32 | (2006.01) |
| H01H 13/85 | (2006.01) |
| H01H 36/00 | (2006.01) |
| A61B 17/00 | (2006.01) |

(52) U.S. Cl.
CPC ............ *A61B 17/068* (2013.01); *A61B 17/32* (2013.01); *H01H 13/85* (2013.01); *H01H 36/008* (2013.01); *A61B 2017/00039* (2013.01); *A61B 2017/00398* (2013.01); *A61B 2017/00464* (2013.01); *H01H 2215/004* (2013.01)

(58) Field of Classification Search
CPC .............. H03K 17/97; H01H 11/0056; H01H 2300/014; H01H 9/06

USPC .......... 200/315; 227/175.1, 180.1, 176.1, 19, 227/178.1, 179.1, 181.1, 175.2, 177.1, 227/182.1

See application file for complete search history.

(56) References Cited

U.S. PATENT DOCUMENTS

| | | | |
|---|---|---|---|
| 4,196,348 | A | 4/1980 | Iwakiri et al. |
| 4,803,362 | A | 2/1989 | Butts |
| 5,321,311 | A | 6/1994 | Umemura et al. |
| 6,013,991 | A | 1/2000 | Philipp |
| 6,517,565 | B1 | 2/2003 | Whitman et al. |
| 7,819,896 | B2 | 10/2010 | Racenet |
| 8,061,576 | B2 | 11/2011 | Cappola |
| 2005/0006434 | A1 | 1/2005 | Wales et al. |

(Continued)

FOREIGN PATENT DOCUMENTS

| | | |
|---|---|---|
| CN | 101227187 A | 7/2008 |
| CN | 203014768 U | 6/2013 |

(Continued)

OTHER PUBLICATIONS

European Search Report dated Feb. 25, 2016, corresponding to European Application No. 15190752.4; 8 pages.

*Primary Examiner* — Ahmed M Saeed

(57) ABSTRACT

An adapter assembly includes a housing, an elongate shaft, and a switch assembly. The switch assembly is partially disposed within the housing and includes a finger switch, and a biasing assembly engaged to the finger switch. The finger switch is pivotably coupled to the housing between an inactivated position and an activated position. The finger switch has a distal portion, and a proximal portion having a magnet configured to activate a sensor of the handle assembly upon movement of the finger switch to the activated position. The biasing assembly biases the finger switch toward the inactivated position.

22 Claims, 3 Drawing Sheets

(56) References Cited

U.S. PATENT DOCUMENTS

| | | | |
|---|---|---|---|
| 2009/0095790 A1 | 4/2009 | Whitman et al. | |
| 2010/0171026 A1 | 7/2010 | Saitou et al. | |
| 2011/0121049 A1 | 5/2011 | Malinouskas et al. | |
| 2011/0204119 A1 | 8/2011 | McCuen | |
| 2012/0089131 A1 | 4/2012 | Zemlok et al. | |
| 2012/0253329 A1 | 10/2012 | Zemlok et al. | |
| 2012/0296159 A1 | 11/2012 | Kanazawa et al. | |
| 2012/0296316 A1 | 11/2012 | Imuta | |
| 2013/0184730 A1 | 7/2013 | Beardsley et al. | |
| 2013/0324978 A1 | 12/2013 | Nicholas et al. | |
| 2014/0012238 A1 | 1/2014 | Chen et al. | |
| 2014/0114403 A1 | 4/2014 | Dale et al. | |
| 2014/0246477 A1 | 9/2014 | Koch, Jr. et al. | |
| 2015/0235789 A1 | 8/2015 | Calderoni | |

FOREIGN PATENT DOCUMENTS

| | | | |
|---|---|---|---|
| KR | 20020020332 A | 3/2002 | |
| KR | 20070000199 U | 2/2007 | |
| WO | 2008147415 A1 | 12/2008 | |
| WO | 2009/039506 A1 | 3/2009 | |

SURGICAL INSTRUMENTS AND SWITCH ASSEMBLIES THEREOF

CROSS-REFERENCE TO RELATED APPLICATIONS

This application claims the benefit of and priority to U.S. Provisional Patent Application No. 62/271,081 filed Dec. 22, 2015, the entire disclosure of which is incorporated by reference herein.

BACKGROUND

1. Technical Field

The present disclosure relates to surgical instruments. More specifically, the present disclosure relates to switch assemblies for use with hand-held electromechanical surgical instruments to actuate various functions of surgical attachments, such as, for example, surgical loading units. Hand-held electromechanical surgical instruments and adapter assemblies for connecting surgical loading units to handle assemblies are also described.

2. Background of Related Art

A number of handle assembly manufacturers have developed product lines with proprietary drive systems for operating and/or manipulating electromechanical surgical instruments. In many instances the electromechanical surgical instruments included a handle assembly, which is reusable, and disposable loading units and/or single use loading units, such as, for example, surgical loading units that were selectively connected to an adapter assembly. The adapter assembly was connected to the handle assembly prior to use and then disconnected from the handle assembly following use in order to be disposed of or in some instances sterilized for re-use.

Handle assemblies include various switches used to actuate one or more functions of a surgical loading unit. Many functions to be performed by a surgical loading unit are specific to that surgical loading unit and a particular adapter assembly designed for use with that selected surgical loading unit. Thus, regardless of the adapter assembly and surgical loading unit combination coupled to the handle assembly, the handle assembly has all of the switches necessary to activate functions of many different types of surgical loading units. That is, upon selection and connection of a particular adapter assembly and surgical loading unit to the handle assembly, the handle assembly may have one or more switches not designed to operate a function of that selected surgical loading unit, thereby making for a more cluttered handle assembly.

Accordingly, it is desirable to provide a surgical instrument capable of actuating the functions of a plurality of interchangeable adapter assemblies and surgical loading units without cluttering the reusable handle assembly with unnecessary switches.

SUMMARY

According to one aspect of the present disclosure, an adapter assembly of a handheld electromechanical surgical device is provided. The adapter assembly includes a housing, an elongate shaft, and a switch assembly. The housing has a distal end, and a proximal end configured to be coupled to a handle assembly of the handheld electromechanical surgical device. The elongate shaft has a proximal end and a distal end. The proximal end of the elongate shaft is coupled to the distal end of the housing, and the distal end of the elongate shaft is configured to be selectively coupled to a surgical loading unit of the handheld electromechanical surgical device. The switch assembly is partially disposed within the housing and includes a finger switch, and a biasing assembly engaged to the finger switch. The finger switch is pivotably coupled to the housing between an inactivated position and an activated position. The finger switch has a distal portion, and a proximal portion having a magnet configured to activate a sensor of the handle assembly upon movement of the finger switch to the activated position. The biasing assembly biases the finger switch toward the inactivated position.

In some embodiments, the finger switch may extend radially outward from a bottom portion of the housing.

It is contemplated that the biasing assembly may have a proximal end having a tapered configuration. The distal portion of the finger switch may have a groove formed therein having the proximal end of the biasing assembly movably disposed therein. The proximal end of the biasing assembly may have a first oblique surface and a second oblique surface. The groove of the finger switch may be defined by a first oblique surface and a second oblique surface. When the finger switch is moved toward the activated position, the first oblique surface of the finger switch may engage the first oblique surface of the biasing assembly to move the biasing assembly in a distal direction. When the finger switch is in the activated position, the second oblique surface of the finger switch may be spaced from the second oblique surface of the biasing assembly. When the finger switch is in the inactivated position, the first and second oblique surfaces of the finger switch may be engaged with the proximal end of the biasing assembly.

It is envisioned that the biasing assembly may include a tubular member, a slider, and a first spring. The tubular member may be secured within the housing. The slider may be movably disposed within the housing and have a proximal end engaged with the distal portion of the finger switch. The slider may have the tubular member disposed therein. The first spring may be disposed between the tubular member and the slider to resiliently bias the slider in a proximal direction relative to the tubular member to resiliently bias the finger switch toward the inactivated position. The biasing assembly may further include a second spring and a tactile switch. The second spring may be disposed within the tubular member and have a proximal end engaged with the slider, and a distal end. The tactile switch may be engaged with the distal end of the second spring such that movement of the slider from a proximal position to a distal position activates the tactile switch to provide tactile feedback that the finger switch is in the activated position.

In some aspects of the present disclosure, the elongate shaft may define a first longitudinal axis, and the proximal portion of the finger switch may define a second longitudinal axis that is parallel with the first longitudinal axis of the elongate shaft when the finger switch is in the inactivated position. The second longitudinal axis of the finger switch may be non-parallel with the first longitudinal axis of the elongate shaft when the finger switch is in the activated position.

In some embodiments, the activated position of the finger switch may include a first activated position in which the magnet is disposed in a first position, and a second activated position, in which the magnet is disposed in a second position located below the first position.

In another aspect of the present disclosure, a hand-held electromechanical surgical instrument is provided. The surgical instrument includes a handle assembly and an adapter assembly. The handle assembly includes a handle housing, a plurality of motors disposed within the handle housing, and a sensor disposed within the handle housing and in communication with one of the motors to actuate the motor. The adapter assembly includes a housing, an elongate shaft, and a switch assembly. The housing has a distal end and a proximal end configured to be coupled to the handle housing. The elongate shaft has a proximal end coupled to the distal end of the housing, and a distal end configured to be coupled to a surgical loading unit. The switch assembly is partially disposed within the housing and includes a finger switch and a biasing assembly. The finger switch is pivotably coupled to the housing between an inactivated position and an activated position. The finger switch has a distal portion, and a proximal portion having a magnet configured to activate the sensor of the handle assembly to effect actuation of the motor upon movement of the finger switch to the activated position. The biasing assembly is engaged to the distal portion of the finger switch to bias the finger switch toward the inactivated position.

In some embodiments, the activated position of the finger switch includes a first activated position and a second activated position. In the first activated position, the magnet is disposed in a first position to effect movement of a drive of the motor in a first direction. In the second activated position, the magnet is disposed in a second position located below the first position to effect movement of the drive of the motor in a second direction, opposite the first direction.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1A:
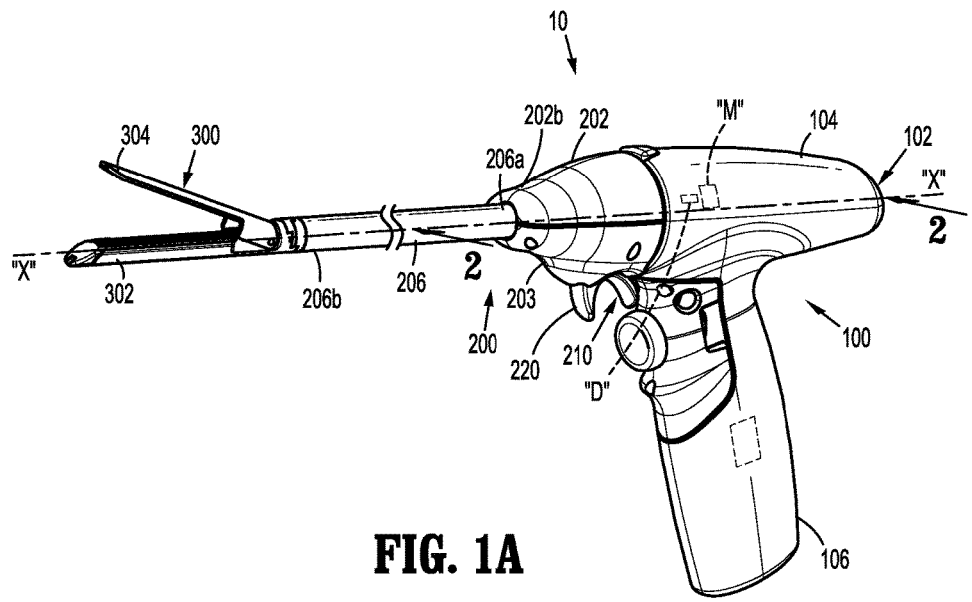
FIG. 1A is a perspective view of a hand-held electromechanical surgical instrument, including a handle assembly, and an adapter assembly connected with the handle assembly, in accordance with an embodiment of the present disclosure.

Embodiments of the presently disclosed surgical instruments including handle assemblies, adapter assemblies and switch assemblies thereof, and surgical loading units are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

A surgical instrument, in accordance with an embodiment of the present disclosure, is generally designated as 10, and is in the form of a powered hand-held electromechanical surgical instrument configured for use with a plurality of different adapter assemblies and/or surgical loading units. The surgical loading units may be for any type of surgical instrument including, but not limited to, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, and a fluid delivery device. Each of the surgical loading units is configured for actuation and manipulation by a handle assembly of the powered hand-held electromechanical surgical instrument 10.

For a detailed discussion of the construction and operation of a surgical loading unit to be coupled with the handle assembly, reference may be made to U.S. Pat. No. 7,819, 896, filed on Aug. 31, 2009, entitled "TOOL ASSEMBLY FOR A SURGICAL STAPLING DEVICE," the entire content of which is incorporated herein by reference.

Figure 1B:
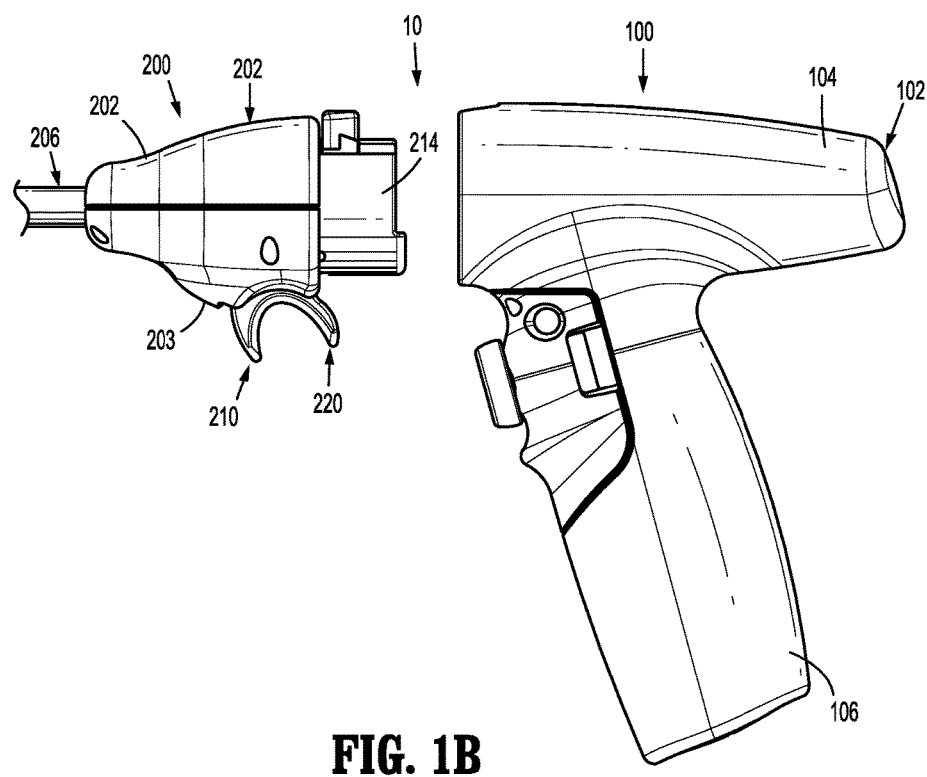
FIG. 1B is a side view of the surgical instrument of FIG. 1A illustrating the adapter assembly and the handle assembly separated from one another.

As illustrated in FIGS. 1A and 1B, hand-held electromechanical surgical instrument 10 includes a handle assembly 100 configured for selective connection with an adapter assembly 200, and, in turn, adapter assembly 200 is configured for selective connection with a surgical loading unit 300, which is configured to perform various surgical functions. Handle assembly 100 is configured and adapted to actuate the various functions of the surgical loading unit 300.

Handle assembly 100 includes a handle housing 102 consisting of a body 104 and a handle portion 106 extending substantially perpendicularly from body 104. Body 104 of handle housing 102 has a plurality of motors "M" situated therein. Motors "M" are each electrically connected (e.g., wirelessly connected) to a motor controller circuit board (not shown) and a battery (not shown) each disposed within handle housing 102.

Each of motors "M" includes a respective motor shaft or drive "D" extending therefrom. Each motor shaft "D" may have a tri-lobe transverse cross-sectional profile for transmitting rotative forces or torque. The motor shafts "D" of motors "M" are non-rotatably received in respective drive connector sleeves (not shown) of adapter assembly 200. Rotation of motor shafts "D" by respective motors "M" function to drive shafts and/or gear components of adapter assembly 200 in order to perform the various operations of surgical loading unit 300. In particular, motors "M" are configured to drive shafts and/or gear components of adapter assembly 200 in order to selectively actuate functions of surgical loading unit 300, for example, to articulate surgical loading unit 300 relative to adapter assembly 200, to rotate surgical loading unit 300 about a longitudinal axis "X" defined by adapter assembly 200 (FIG. 1A), to move a cartridge assembly 302 of surgical loading unit 300 relative to an anvil assembly 304 of surgical loading unit 300, extend a knife blade (not shown) of surgical loading unit 300, and/or to fire staples from within cartridge assembly 302 of surgical loading unit 300.

Figure 2:
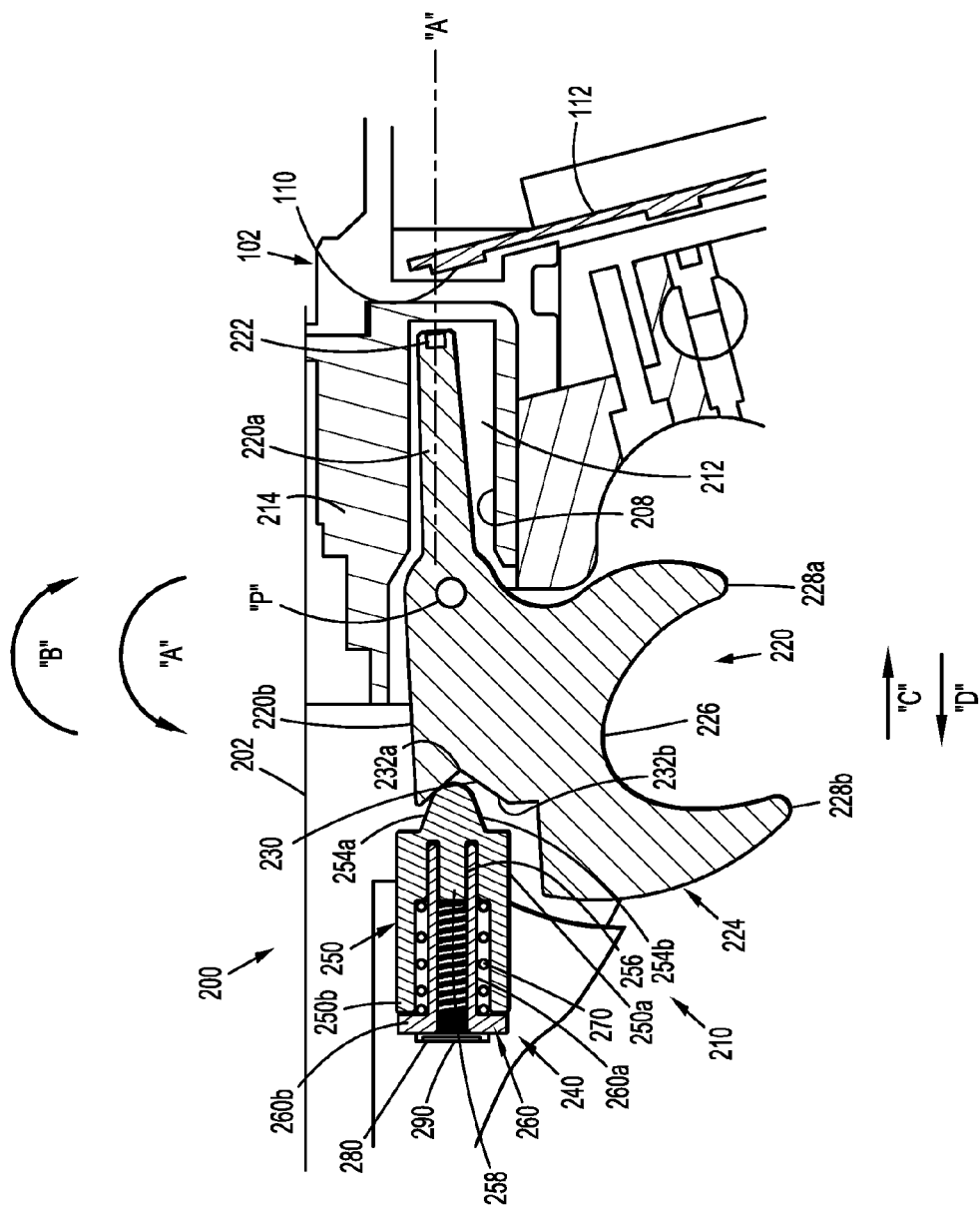
FIG. 2 is an enlarged, cross-sectional view, taken along line 2-2 of FIG. 1A, of the surgical instrument illustrating a switch assembly thereof.

With reference to FIGS. 1A, 1B, and 2, handle portion 106 of handle housing 102 has a sensor, such as, for example, a hall effect sensor 110 situated therein. Hall effect sensor 110 senses a movement of a magnet 222 of a switch assembly 210 to control the operation of one of motors "M" and, in turn, the functions of surgical loading unit 300, as described in detail below. Hall effect sensor 110 is in communication (e.g., via a wireless connection) with the motor controller circuit board (not shown) of handle assembly 100 to signal to the motor controller circuit board that the motor "M" is to be actuated. While hall effect sensors 110 are shown and described, it is contemplated and within the scope of the present disclosure for any type of sensor to be used, including and not limited to tactile, pressure or optical sensors, to tactile, pressure or optical switches, or the like.

Hall effect sensor 110 is disposed on a printed circuit board 112 situated within handle housing 102. Printed circuit board 112 has a battery (not shown) mounted thereto that supplies power to motors "M." An inductor (not shown) may be connected to printed circuit board 112 and is configured to wirelessly transmit power generated by the battery to any of the electrical components of surgical instrument 10, including motors "M," to drive the operation of surgical loading unit 300. For example, the battery, via the inductor, may transmit power to motors "M" by one of direct induction or resonant magnetic induction. In some embodiments, the battery may be physically connected to motors "M" using wires. It is contemplated that more than one hall effect sensor may be supported on the printed circuit board 112.

For a detailed description of the construction and operation of an exemplary electromechanical, hand-held, powered surgical instrument, reference may be made to International Publication No. WO 2009/039506, filed on Sep. 22, 2008, and U.S. Patent Application Publication No. 2011/0121049, filed on Nov. 20, 2009, the entire contents of each of which are incorporated herein by reference.

With continued reference to FIGS. 1A and 1B, adapter assembly 200 is configured to couple surgical loading unit 300 to handle assembly 100. Adapter assembly 200 includes a housing 202 and an elongate shaft 206 extending distally from a distal end 202*b* of housing 202. Housing 202 and elongate shaft 206 are configured and dimensioned to house the components of adapter assembly 200. Elongate shaft 206 defines a longitudinal axis "X" and is dimensioned for endoscopic insertion. For example, elongate shaft 206 is passable through a typical trocar port, cannula, or the like. Housing 202 is dimensioned to not enter the trocar port, cannula, or the like. Elongate shaft 206 of adapter assembly 200 has a proximal end 206*a* configured to be coupled to housing 202 of adapter assembly 200 and a distal end 206*b* configured to be coupled to surgical loading unit 300. Adapter assembly 200 converts a rotation of drive elements (not shown) of handle assembly 100 into axial movement of driven members (not shown) of adapter assembly 200 to actuate functions of surgical loading unit 300.

An exemplary embodiment of an adapter assembly is disclosed in U.S. Patent Application Publication No. 2013/0324978, filed on May 2, 2013, the entire contents of which are incorporated by reference herein.

Figure 3:
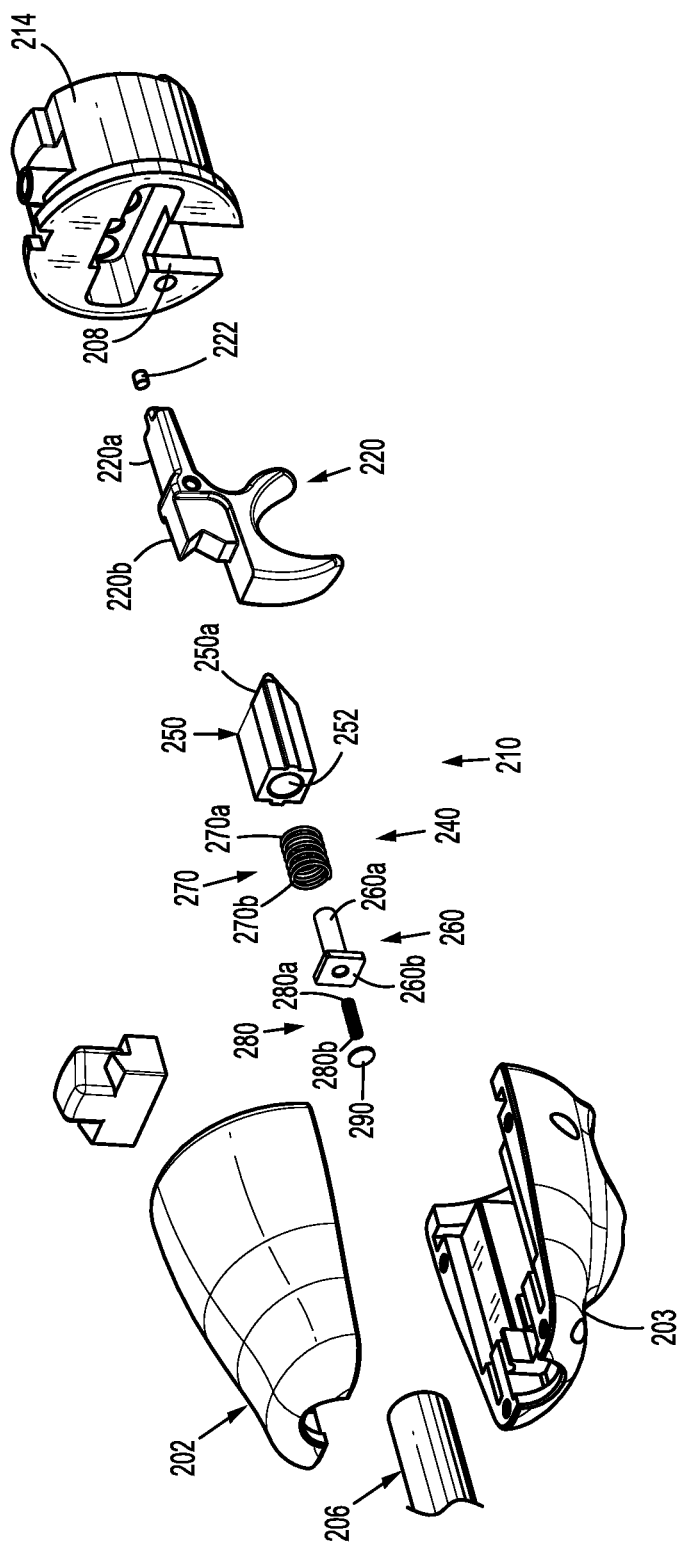
FIG. 3 is a perspective view, with parts separated, of the adapter assembly and components of the switch assembly of FIG. 2.

With reference to FIGS. 2 and 3, adapter assembly 200 includes a switch assembly 210 partially disposed within housing 202. Switch assembly 210 is configured to actuate functions of surgical loading unit 300 (FIG. 1A). Switch assembly 210 is in operative mechanical and/or electrical communication with a motor of motors "M" via hall effect sensor 110. As such, when a user actuates switch assembly 210 of adapter assembly 200, a respective one of motors "M" is activated and, in turn, actuates a function performed by surgical loading unit 300 that is assigned to switch assembly 210, as described in greater detail below.

Switch assembly 210 of adapter assembly 200 generally includes a finger switch 220 and a biasing assembly 240 that are operably engaged to one another. Finger switch 220 is pivotably coupled to an inner surface 208 of housing 202 of adapter assembly 200 and pivotable relative thereto about a pivot point "P." Finger switch 220 has a proximal portion 220*a* and a distal portion 220*b* with the pivot point "P" being disposed therebetween. Proximal portion 220*a* of finger switch 220 is in the form of a shaft or arm that defines a longitudinal axis "Z" and is situated within a channel 212 defined in an inner housing 214 of adapter assembly 200. Proximal portion 220*a* of finger switch 220 has a magnet 222 attached to or disposed within a proximal-most end thereof. In some embodiments, magnet 222 may be disposed at a variety of locations along proximal portion 220*a* of finger switch 220. Magnet 222 is configured to activate hall effect sensor 110 of handle assembly 100 to effect actuation of the motor "M" upon movement of finger switch 220 between an inactivated position and at least one activated position.

Distal portion 220*b* of finger switch 220 has a bottom portion 224 that defines an arcuate indentation 226 therein configured for receipt of a finger of a user. As such, bottom portion 224 of finger switch 220 has two curved prongs 228*a*, 228*b* that extend radially outward from a bottom portion 203 (FIGS. 1A and 1B) of housing 202 of adapter assembly 200. To move finger switch 220 from an inactivated position to one of a first or second activated positions, a finger of a clinician is positioned within indentation 226 of finger switch 220 and a force is applied in either a proximal direction on proximal prong 228*a* of finger switch 220 or a distal direction on distal prong 228*b* of finger switch 220.

Specifically, an application of a force on proximal prong 228*a*, oriented in a proximal direction, rotates finger switch 220 about pivot point "P," in a direction indicated by arrow "A" (counter-clockwise) in FIG. 2, to change the position of magnet 222 relative to hall effect sensor 110. An application of a force on distal prong 228*b*, oriented in a distal direction, rotates finger switch 220 about pivot point "P," in a direction indicated by arrow "B" (clockwise) in FIG. 2, to change the position of magnet 222 relative to hall effect sensor 110. Upon movement of finger switch 220 from the inactivated position to one of the first or second activated positions, longitudinal axis "Z" of proximal portion 220*a* of finger switch 220 is moved from being parallel with longitudinal axis "X" of elongate shaft 206 (FIG. 1A) of adapter assembly 200, to being non-parallel (i.e., angled) relative to longitudinal axis "X" of elongate shaft 206. Other movements of finger switch 220 relative to elongate shaft 206 are contemplated and within the scope of the present disclosure.

Distal portion 220*b* of finger switch 220 has a groove 230 formed therein that is configured for operable receipt of biasing assembly 240 of switch assembly 210. Groove 230 is defined by an inner surface of distal portion 220*b* of finger switch 220 that includes a first or top oblique 232*a* surface and a second or bottom oblique surface 232*b* that extends at an acute angle relative to first oblique surface 232*a*. As such, groove 230 has a V-shaped configuration. In some embodiments, groove 230 may assume a variety of shapes configured for operable receipt of biasing assembly 240, such as, for example, U-shaped, squared, or the like.

With continued reference to FIGS. 2 and 3, biasing assembly 240 of switch assembly 210 is disposed within housing 202 of adapter assembly 200 and distally of finger switch 220. Biasing assembly 240 is engaged to distal portion 220*b* of finger switch 220 to bias finger switch 220 toward the inactivated position. Biasing assembly 240 includes a slider 250, a tubular member 260, and a first spring 270. Slider 250 is movably disposed within housing 202 and has a generally rectangular shape, but it is contemplated that slider 250 may assume any suitable shape. Slider 250 has a proximal end 250a and a distal end 250b and defines a bore 252 that extends from distal end 250b toward proximal end 250a and is configured for receipt of tubular member 260. Proximal end 250a of slider 250 has a tapered configuration such that proximal end 250a of slider 250 has a first or top oblique surface 254a and a second or bottom oblique surface 254b that each terminate at a flattened proximal tip of slider 250. First oblique surface 254a of slider 250 is disposed adjacent to first oblique surface 232a of finger switch 220, and second oblique surface 254b of slider 250 is disposed adjacent to second oblique surface 232b of finger switch 220. First and second oblique surfaces 254a, 254b of slider 250 interplay with respective first and second oblique surfaces 232a, 232b of finger switch 220 to maintain finger switch 220 in the inactivated position, as will be described in further detail below.

Proximal end 250a of slider has an annular recess 256 formed therein configured for slidable receipt of tubular member 260. Annular recess 256 is in communication with bore 252 of slider 250 and defines a plug 258 that is received within tubular member 260. Tubular member 260 of biasing assembly 240 is secured within housing 202 of adapter assembly 200 and prevented from moving longitudinally within housing 202. Tubular member 260 has a base portion 260b fixed within housing 202, and a tube or cannulated shaft 260a extending perpendicularly from base portion 260b. Cannulated shaft 260a of tubular member 260 extends within bore 252 of slider 250 and plug 258 of slider 250 is slidably disposed within a proximal end of cannulated shaft 260a. First spring 270 is disposed about cannulated shaft 260a of tubular member 260 and within bore 252 of slider 250. First spring 270 has a proximal end 270a engaged to or fixed with proximal end 250a of slider 250, and a distal end 270b engaged to base portion 260b of tubular member 260 to resiliently bias slider 250 in a proximal direction relative to tubular member 260. As such, since proximal end 250a of slider 250 is in abutment with finger switch 220, the proximally-oriented bias of first spring 270 of biasing assembly 240 applies a constant proximally-oriented bias on finger switch 220 to maintain finger switch 220 in the inactivated position.

Biasing assembly 240 further includes a second spring 280 and a tactile or dome switch 290 that provides tactile feedback to a clinician when finger switch 220 has achieved either of the first or second activated positions. Second spring 280 is disposed within tubular member 260 and has a proximal end 280a and a distal end 280b. Proximal end 280a of second spring 280 is engaged to plug 258 of slider 250. Distal end 280b of second spring 280 is engaged to dome switch 290 such that upon distal movement of slider 250 relative to tubular member 260, plug 258 of slider 250 compresses second spring 280 to effect an activation or compression of dome switch 290, which can be felt by a clinician during use of finger switch 220.

In use, to move finger switch 220 from the inactivated position to the first activated position, a force is applied to finger switch 220, in the direction indicated by arrow "C" in FIG. 2 (i.e., proximally), to rotate finger switch 220, in the direction indicated by arrow "A." As finger switch 220 begins to rotate, first oblique surface 232a of finger switch 220 cams against first oblique surface 254a of slider 250 of biasing assembly 240 to overcome the proximally-oriented bias of first spring 270 of biasing assembly 240 and moves slider 250 of biasing assembly 240 distally. Continued rotation of finger switch 220 toward the first activated position ultimately activates dome switch 290 of biasing assembly 240 via the compression of second spring 280 of biasing assembly 240, indicating to the clinician that finger switch 220 is in the first activated position. Upon finger switch 220 rotating to the first activated position, second oblique surface 232b of finger switch 220 becomes spaced from second oblique surface 254b of slider 250.

In the first activated position, magnet 222 of finger switch 220 is disposed in a first position, as shown in FIG. 2, which is sensed by hall effect sensor 110 of handle assembly 100. In particular, hall effect sensor 110 senses a change in the magnetic flux as magnet 222 moves to the first position and relays a message or signal to the motor controller circuit board of handle assembly 100 to actuate motor "M" (FIG. 1A) and effect rotation of the drive "D" of motor "M" in a first direction. The actuation of motor "M" effects an operation of surgical loading unit 300, for example, a closing of jaw members 302, 304 (FIG. 1A), an articulation of surgical loading unit 300, supplying of energy (e.g., electrosurgical energy) to surgical loading unit 300, and/or an actuation of a knife blade (not shown) of surgical loading unit 300.

The force applied to finger switch 220 is removed to allow finger switch 220 to return to the inactivated position. In particular, upon removing the force applied to finger switch 220, the proximally-oriented bias supplied by first spring 270 on slider 250 of biasing assembly 240 causes first oblique surface 254a of slider 250 to cam against first oblique surface 232a of finger switch 220, which causes finger switch 220 to move proximally to the inactivated position. When finger switch 220 is in the inactivated position, longitudinal axis "Z" of proximal portion 220a of finger switch 220 is parallel with longitudinal axis "X" of elongate shaft 206 of adapter assembly 200 and first and second oblique surfaces 254a, 254b of slider 250 are each in abutment with respective first and second oblique surfaces 232a, 232b of finger switch 220 to maintain finger switch 220 in the inactivated position. Hall effect sensor 110 of handle assembly 100 senses that magnet 222 has returned to the inactivated or home position and inactivates motor "M."

To move finger switch 220 from the inactivated position to the second activated position, a force is applied to finger switch 220, in the direction indicated by arrow "D" in FIG. 2 (i.e., distally), to rotate finger switch 220, in the direction indicated by arrow "B." As finger switch 220 begins to rotate, second oblique surface 232b of finger switch 220 cams against second oblique surface 254b of slider 250 of biasing assembly 240 to overcome the proximally-oriented bias of first spring 270 of biasing assembly 240 and moves slider 250 of biasing assembly 240 distally. Continued rotation of finger switch 220 toward the second activated position ultimately activates dome switch 290 of biasing assembly 240 via the compression of second spring 280 of biasing assembly 240, indicating to the clinician that finger switch 220 is in the second activated position. Upon finger switch 220 rotating to the second activated position, first oblique surface 232a of finger switch 220 becomes spaced from first oblique surface 254a of slider 250.

In the second activated position, magnet 222 is disposed in a second position (not shown), which is sensed by hall effect sensor 110 of handle assembly 100. When hall effect sensor 110 senses that magnet 222 of switch assembly 210 is moved to the second position, sensor 110 communicates with motor "M" to actuate motor "M" and effect rotation of the drive "D" of motor "M" in a second direction, opposite the first direction in which drive "D" is moved when finger switch 220 is in the first activated position. The actuation of drive "D" of motor "M" by finger switch 220 being moved to the second activated position effects a reverse operation of surgical loading unit 300 from that effected during movement of the finger switch 220 to the first activated position. For example, jaw members 302, 304 of surgical loading unit 300 may be opened, surgical loading unit 300 may be articulated back to a parallel or axially aligned position, and/or the knife blade (not shown) may be retracted. In some embodiments, actuation of motor "M," via moving finger switch 220 to the second activated position, effects a different operation of surgical loading unit 300 than when finger switch 220 is moved to the first activated position.

In some embodiments, switch assembly 210 may be assigned to actuate various functions to be carried out by various surgical loading units.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed surgical instruments including switch assemblies. Therefore, the above description should not be construed as limiting, but merely as exemplifications of embodiments. Those skilled in the art will envision other modifications within the scope and spirit of the present disclosure.

The invention claimed is:

1. An adapter assembly, comprising:
   a housing having a distal end, and a proximal end configured to be coupled to a handle assembly of a handheld electromechanical surgical device;
   an elongate shaft having a proximal end coupled to the distal end of the housing, and a distal end configured to be selectively coupled to a surgical loading unit; and
   a switch assembly partially disposed within the housing and including:
      a finger switch pivotably coupled to the housing between an inactivated position and at least one activated position, the finger switch having a distal portion, and a proximal portion having a magnet configured to activate a sensor of the handle assembly upon movement of the finger switch to the at least one activated position; and
      a biasing assembly engaged to the finger switch to bias the finger switch toward the inactivated position, wherein the switch assembly is partially disposed within the housing when the housing is unattached from the handle assembly.

2. The adapter assembly according to claim 1, wherein a portion of the finger switch is disposed within a bottom portion of the housing.

3. The adapter assembly according to claim 1, wherein the biasing assembly has a proximal end having a tapered configuration, and wherein the distal portion of the finger switch has a groove formed therein having the proximal end of the biasing assembly movably disposed therein.

4. The adapter assembly according to claim 3, wherein the proximal end of the biasing assembly has a first oblique surface and a second oblique surface, the groove of the finger switch being defined by a first oblique surface and a second oblique surface, and wherein when the finger switch is moved toward the at least one activated position, the first oblique surface of the finger switch engages the first oblique surface of the biasing assembly to move the biasing assembly in a distal direction.

5. The adapter assembly according to claim 4, wherein when the finger switch is in the at least one activated position, the second oblique surface of the finger switch is spaced from the second oblique surface of the biasing assembly.

6. The adapter assembly according to claim 4, wherein when the finger switch is in the inactivated position, the first and second oblique surfaces of the finger switch are engaged with the proximal end of the biasing assembly.

7. The adapter assembly according to claim 1, wherein the biasing assembly includes:
   a tubular member secured within the housing;
   a slider movably disposed within the housing and having a proximal end engaged with the distal portion of the finger switch, the slider having the tubular member disposed therein; and
   a first spring disposed between the tubular member and the slider to resiliently bias the slider in a proximal direction relative to the tubular member to resiliently bias the finger switch toward the inactivated position.

8. The adapter assembly according to claim 7, wherein the biasing assembly further includes:
   a second spring disposed within the tubular member and having a proximal end engaged with the slider, and a distal end; and
   a tactile switch engaged with the distal end of the second spring such that movement of the slider from a proximal position to a distal position activates the tactile switch to provide tactile feedback that the finger switch is in the at least one activated position.

9. The adapter assembly according to claim 1, wherein the elongate shaft defines a first longitudinal axis, and the proximal portion of the finger switch defines a second longitudinal axis that is parallel with the first longitudinal axis of the elongate shaft when the finger switch is in the inactivated position and is non-parallel with the first longitudinal axis of the elongate shaft when the finger switch is in the at least one activated position.

10. The adapter assembly according to claim 1, wherein the at least one activated position of the finger switch includes a first activated position in which the magnet is disposed in a first position, and a second activated position, in which the magnet is disposed in a second position located below the first position.

11. The adapter assembly according to claim 1, wherein the housing of the adapter assembly defines an inner chamber therein, the switch assembly being partially disposed within the inner chamber of the housing.

12. A hand-held electromechanical surgical instrument, comprising:
   a handle assembly including:
      a handle housing;
      a plurality of motors disposed within the handle housing; and
      a sensor disposed within the handle housing and in communication with at least one of the plurality of motors to actuate the at least one of the plurality of motors; and
   an adapter assembly including:
      a housing having a distal end and a proximal end configured to be coupled to the handle housing;
      an elongate shaft having a proximal end coupled to the distal end of the housing, and a distal end configured to be coupled to a surgical loading unit; and
      a switch assembly partially disposed within the housing and including:
         a finger switch pivotably coupled to the housing between an inactivated position and at least one activated position, the finger switch having a distal portion, and a proximal portion having a magnet configured to activate the sensor of the handle assembly to effect actuation of the at least one of the plurality of motors upon movement of the finger switch to the at least one activated position; and a biasing assembly engaged to the finger switch to bias the finger switch toward the inactivated position, wherein the switch assembly is partially disposed within the housing when the housing is unattached from the handle assembly.

13. The hand-held surgical instrument according to claim 12, wherein a portion of the finger switch of the adapter assembly is disposed within a bottom portion of the housing.

14. The hand-held surgical instrument according to claim 12, wherein the biasing assembly of the adapter assembly has a proximal end having a tapered configuration, and wherein the distal portion of the finger switch has a groove formed therein having the proximal end of the biasing assembly movably disposed therein.

15. The hand-held surgical instrument according to claim 14, wherein the proximal end of the biasing assembly has a first oblique surface and a second oblique surface, the groove of the finger switch being defined by a first oblique surface and a second oblique surface, and wherein when the finger switch is moved toward the at least one activated position, the first oblique surface of the finger switch engages the first oblique surface of the biasing assembly to move the biasing assembly in a distal direction.

16. The hand-held surgical instrument according to claim 15, wherein when the finger switch is in the at least one activated position, the second oblique surface of the finger switch is spaced from the second oblique surface of the biasing assembly.

17. The hand-held surgical instrument according to claim 15, wherein when the finger switch is in the inactivated position, the first and second oblique surfaces of the finger switch are engaged with the proximal end of the biasing assembly.

18. The hand-held surgical instrument according to claim 12, wherein the biasing assembly includes:
a tubular member secured within the housing;
a slider movably disposed within the housing and having a proximal end engaged with the distal portion of the finger switch, the slider having the tubular member disposed therein; and
a first spring disposed between the tubular member and the slider to resiliently bias the slider in a proximal direction relative to the tubular member to resiliently bias the finger switch toward the inactivated position.

19. The hand-held surgical instrument according to claim 18, wherein the biasing assembly of the adapter assembly further includes:
a second spring disposed within the tubular member and having a proximal end engaged with the slider, and a distal end; and
a tactile switch engaged with the distal end of the second spring such that movement of the slider from a proximal position to a distal position activates the tactile switch to provide tactile feedback that the finger switch is in the at least one activated position.

20. The hand-held surgical instrument according to claim 12, wherein the elongate shaft defines a first longitudinal axis, and the proximal portion of the finger switch defines a second longitudinal axis that is parallel with the first longitudinal axis of the elongate shaft when the finger switch is in the inactivated position and is non-parallel with the first longitudinal axis of the elongate shaft when the finger switch is in the at least one activated position.

21. The hand-held surgical instrument according to claim 12, wherein the at least one activated position of the finger switch includes a first activated position in which the magnet is disposed in a first position to effect movement of a drive of the motor in a first direction, and a second activated position, in which the magnet is disposed in a second position located below the first position to effect movement of the drive of the motor in a second direction, opposite the first direction.

22. The hand-held surgical instrument according to claim 12, wherein the housing of the adapter assembly defines an inner chamber therein, the switch assembly being partially disposed within the inner chamber of the housing.

* * * * *